US 6,668,195 B2

(12) United States Patent
Warman et al.

(10) Patent No.: US 6,668,195 B2
(45) Date of Patent: Dec. 23, 2003

(54) METHODS AND APPARATUS FOR REDUCING THE LIKELIHOOD OF ATRIAL FIBRILLATION

(75) Inventors: Eduardo N. Warman, Maple Grove, MN (US); H. Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 79 days.

(21) Appl. No.: 10/003,936

(22) Filed: Oct. 30, 2001

(65) Prior Publication Data

US 2003/0083706 A1 May 1, 2003

(51) Int. Cl.[7] .............................................. A61N 1/362
(52) U.S. Cl. ........................................................ 607/14
(58) Field of Search .............................. 607/4, 9, 5, 14

(56) References Cited

U.S. PATENT DOCUMENTS

| | | | |
|---|---|---|---|
| 4,059,116 A | 11/1977 | Adams .................. | 128/419 PG |
| 4,248,238 A | 2/1981 | Joseph .................. | 128/419 PG |
| 4,280,502 A | 7/1981 | Baker, Jr. et al. ..... | 128/419 PG |
| 4,284,082 A | 8/1981 | Funke et al. .......... | 128/419 PG |
| 4,312,355 A | 1/1982 | Funke .................. | 128/419 PG |
| 4,343,311 A | 8/1982 | Markowitz ............ | 128/419 PG |
| 4,363,325 A | 12/1982 | Roline et al. ......... | 128/419 PG |
| 4,401,119 A | 8/1983 | Herpers ................ | 128/419 PG |
| 4,407,287 A | 10/1983 | Herpers ................ | 128/419 PG |
| 4,421,116 A | 12/1983 | Markowitz ............ | 128/419 PG |
| 4,428,378 A | 1/1984 | Anderson et al. ..... | 128/419 PG |
| 4,429,697 A | 2/1984 | Nappholz et al. ..... | 128/419 PG |
| 4,452,248 A | 6/1984 | Keller, Jr. ............. | 128/419 PG |
| 4,515,161 A | 5/1985 | Wittkampf et al. ... | 128/419 PG |
| 4,523,593 A | 6/1985 | Rueter .................. | 128/419 PG |
| 4,527,568 A | 7/1985 | Rickards ............... | 128/419 PG |
| 4,541,430 A | 9/1985 | Elmqvist et al. ...... | 128/419 PG |
| 4,554,921 A | 11/1985 | Boute et al. .......... | 128/419 PG |
| 4,574,437 A | 3/1986 | Segerstad et al. ..... | 128/419 PG |
| 4,624,260 A | 11/1986 | Baker, Jr. et al. ..... | 128/419 PG |
| 4,714,079 A | 12/1987 | Hedberg et al. ...... | 128/419 PG |
| 4,738,250 A | 4/1988 | Fulkerson et al. .......... 128/421 |
| 4,890,617 A | 1/1990 | Markowitz et al. ... | 128/419 PG |
| 4,998,974 A | 3/1991 | Aker .................... | 128/419 PG |
| 5,086,772 A | 2/1992 | Larnard et al. ......... | 128/419 D |
| 5,107,850 A | 4/1992 | Olive .......................... 128/705 |
| 5,133,350 A | 7/1992 | Duffin .................. | 128/419 PG |
| 5,144,947 A | 9/1992 | Wilson ................. | 128/419 PG |
| 5,144,949 A | 9/1992 | Olson ................... | 128/419 PG |
| 5,154,172 A | 10/1992 | Terry, Jr. et al. ........ | 128/419 R |
| 5,193,550 A | 3/1993 | Duffin ......................... 128/697 |
| 5,215,089 A | 6/1993 | Baker, Jr. .................... 128/642 |
| 5,335,657 A | 8/1994 | Terry, Jr. et al. .............. 607/45 |
| 5,356,425 A | 10/1994 | Bardy et al. .................. 607/14 |
| 5,374,280 A | 12/1994 | den Dulk ...................... 607/14 |
| 5,391,185 A | 2/1995 | Kroll ............................ 607/4 |
| 5,395,397 A * | 3/1995 | Lindgren et al. .............. 607/9 |
| 5,403,356 A | 4/1995 | Hill et al. ..................... 607/14 |
| 5,411,524 A | 5/1995 | Rahul ............................ 607/4 |
| 5,480,413 A | 1/1996 | Greenhut et al. ............. 607/14 |
| 5,522,852 A | 6/1996 | White et al. ................... 607/5 |
| 5,549,642 A | 8/1996 | Min et al. ...................... 607/5 |

(List continued on next page.)

Primary Examiner—George R. Evanisko
(74) Attorney, Agent, or Firm—Girma Wolde-Michael; Daniel G. Chapik

(57) ABSTRACT

Methods and apparatus for reducing the incidence of atrial fibrillation includes selecting a desired ventricular rate, pacing the ventricle of the heart at the desired ventricular rate, and pacing the atrium of the heart at twice the desired ventricular rate while the desired ventricular rate is less than a preferred rate. Some methods of the present invention include pacing the atrium of the heart at the desired ventricular rate while the desired ventricular rate is greater than the preferred rate. Other methods of the present invention include pacing the atrium of the heart at a predetermined/preferred atrial rate while the desired ventricular rate is greater than the preferred rate.

18 Claims, 8 Drawing Sheets

U.S. PATENT DOCUMENTS

| | | | |
|---|---|---|---|
| 5,562,708 A | 10/1996 | Combs et al. | 607/4 |
| 5,601,615 A | 2/1997 | Markowitz et al. | 607/28 |
| 5,609,613 A | 3/1997 | Woodson et al. | 607/19 |
| 5,620,468 A | 4/1997 | Mongeon et al. | 607/5 |
| 5,630,834 A | 5/1997 | Bardy | 607/5 |
| 5,674,251 A | 10/1997 | Combs et al. | 607/4 |
| 5,690,686 A | 11/1997 | Min et al. | 607/5 |
| 5,700,282 A | 12/1997 | Zabara | 607/9 |
| 5,792,193 A | 8/1998 | Stoop | 607/14 |
| 5,814,083 A | 9/1998 | Hess et al. | 607/14 |
| 5,840,079 A | 11/1998 | Warman et al. | 607/4 |
| 5,861,012 A | 1/1999 | Stroebel | 607/28 |
| 5,876,422 A | 3/1999 | van Groeningen | 607/3 |
| 5,916,239 A | 6/1999 | Geddes et al. | 607/14 |
| 5,928,271 A | 7/1999 | Hess et al. | 607/14 |
| 5,954,755 A | 9/1999 | Casavant | 607/28 |
| 6,256,537 B1 | 7/2001 | Stoop et al. | 607/14 |
| 6,272,380 B1 | 8/2001 | Warman et al. | 607/5 |
| 6,280,414 B1 | 8/2001 | Shah et al. | 604/104 |
| 6,292,701 B1 | 9/2001 | Prass et al. | 607/116 |
| 6,292,702 B1 | 9/2001 | King et al. | 607/116 |
| 6,526,317 B2 * | 2/2003 | Hsu et al. | 607/4 |

* cited by examiner

METHODS AND APPARATUS FOR REDUCING THE LIKELIHOOD OF ATRIAL FIBRILLATION

FIELD OF THE INVENTION

The present invention relates generally to cardiac pacemakers. More particularly, the present invention relates to cardiac pacemakers for treating atrial fibrillation.

BACKGROUND OF THE INVENTION

An arrhythmia is a heart rhythm disorder which interferes with the life sustaining blood circulation activities of the heart. Examples of arrhythmias include ventricular fibrillation and atrial fibrillation. Ventricular fibrillation affects the lower chambers of the heart (the ventricles) and atrial fibrillation affects the upper chambers of the heart (the atria). Ventricular fibrillation is a rapid and disorganized firing of muscle fibers within the ventricular myocardium. During ventricular fibrillation, the ventricles do not contract in an organized manner, no blood is pumped, and blood pressure falls to zero. Patient death may occur within 4 minutes from the onset of ventricular fibrillation. Companies such as Medtronic, Inc., have developed implantable defibrillators which may be used to successfully treat ventricular fibrillation by delivering a defibrillating shock to the heart when fibrillation is detected.

Atrial fibrillation occurs more frequently than ventricular fibrillation. It has been estimated that atrial fibrillation affects more than million people worldwide. As people age, their chances of developing atrial fibrillation increase dramatically. In fact, approximately 70% of all people with atrial fibrillation are over 65 years of age. Although atrial fibrillation occurs with great frequency, successful therapies for atrial fibrillation have been difficult to identify.

The symptoms of atrial fibrillation may include shortness of breath, loss of the ability to exercise, chest pain, rapid heart beating, light headedness, and loss of consciousness. When atrial fibrillation occurs, the upper chambers of the heart (the atria) rapidly quiver instead of contracting in an organized manner. The atria of the heart may beat/quiver at a rate of between 350 and 600 times per minute during an episode of atrial fibrillation.

Because the pumping function of the upper chambers does not work properly during atrial fibrillation, blood is not completely emptied from the heart's chambers, causing it to stagnate in the upper chambers of the heart. Over time, clots may form in this stagnant blood. Occasionally, clots may break free and enter the blood stream. When one of these blood clots lodges in the blood vessels of the brain, a stroke may result. It has been estimated that atrial fibrillation is responsible for over 70,000 strokes each year. Because treating atrial fibrillation is an important way to prevent strokes from occurring, the American Heart Association has called for aggressive treatment of atrial fibrillation.

SUMMARY OF THE INVENTION

The present invention relates generally to cardiac pacemakers. More particularly, the present invention relates to cardiac pacemakers for treating atrial fibrillation. The structures and methods in accordance with the present invention may be utilized to reduce the likelihood of atrial fibrillation in a heart. One such method comprises the steps of selecting a desired ventricular rate and pacing the ventricle of the heart at this desired ventricular rate.

In certain implementations, the atrium of the heart is paced at twice the desired ventricular rate while the desired ventricular rate is less than a preferred rate. In these advantageous implementations, the atrium of the heart is paced at the desired ventricular rate while the desired ventricular rate is greater than the preferred rate. The preferred rate may be selected to match a particular patient, for example, by taking into account physical characteristics of that patient.

In other implementations, the atrium of the heart is paced at an advantageous atrial rate while the desired ventricular rate is greater than the preferred rate. While the desired ventricular rate is less than the preferred rate, the atrium of the heart may be paced at twice the desired ventricular rate.

In one aspect of the present invention, an atrial pulse is delivered synchronously with each ventricle pulse. In another aspect of the present invention, a ventricular pulse is delivered substantially synchronous with each atrial pulse while the desired ventricular rate is greater than the preferred rate. While the desired ventricular rate is less than the preferred rate, a ventricle pulse may be advantageously delivered synchronously with one out of two atrial pulses. The synchronous arrangement allows an offset between atrial and ventricular pulses.

In certain implementations, the step of selecting the desired ventricular rate may include the steps of sensing spontaneous ventricular signals, and determining a desired ventricular rate in response to the sensed ventricle signals. Methods in accordance with the present invention may include the step of severing a conductive path between the atrium and the ventricle as one of many preferred surgical procedures in implementing one aspect of the present invention. The step of severing the conductive path between the atrium and the ventricle may comprise, for example, the step of ablating an A-V node of the heart.

A pacing system in accordance with the present invention may include a pacemaker having a controller. The controller may comprise, for example, a microprocessor. The controller may direct a ventricular pulse generator of the pacemaker to provide pacing pulses to a ventricle via one or more leads coupled to one or more ventricular electrodes. The controller may also direct an atrial pulse generator to provide pacing pulses to an atrium via one or more leads coupled to one or more atrial electrodes. The atrial pulse generator and the ventricular pulse generator may each include one or more capacitors, and a switching circuit capable of charging the capacitor(s) by coupling the capacitor(s) to an energy source and discharging the capacitor(s) through the electrodes.

A pacemaker in accordance with the present invention may also include a signal processor for sensing and processing spontaneous signals from heart. Spontaneous signals from the heart may be used in determining a desired ventricular rate. In some implementations of the present invention, the signal processor may include one or more amplifiers, and one or more filters. Further rate responses may be established using methods and structures disclosed in U.S. Pat. No. 5,052,388 to Sivula which is incorporated herein in its entirety by reference.

A pacemaker in accordance with the present invention may further include a memory. The memory may be used to store operating instructions for the controller. The memory may also be used to store values in accordance with the present invention. Examples of values that may be stored include a preferred rate and a desired ventricular rate and/or a desired atrial rate. The pacemaker may also include a telemetry antenna. The telemetry antenna may be used in conjunction with the controller to load instructions and values into the memory.

DETAILED DESCRIPTION OF THE PREFERRED EMBODIMENT

The following detailed description should be read with reference to the drawings, in which like elements in different drawings are numbered identically. The drawings, which are not necessarily to scale, depict selected embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

Figure 1:
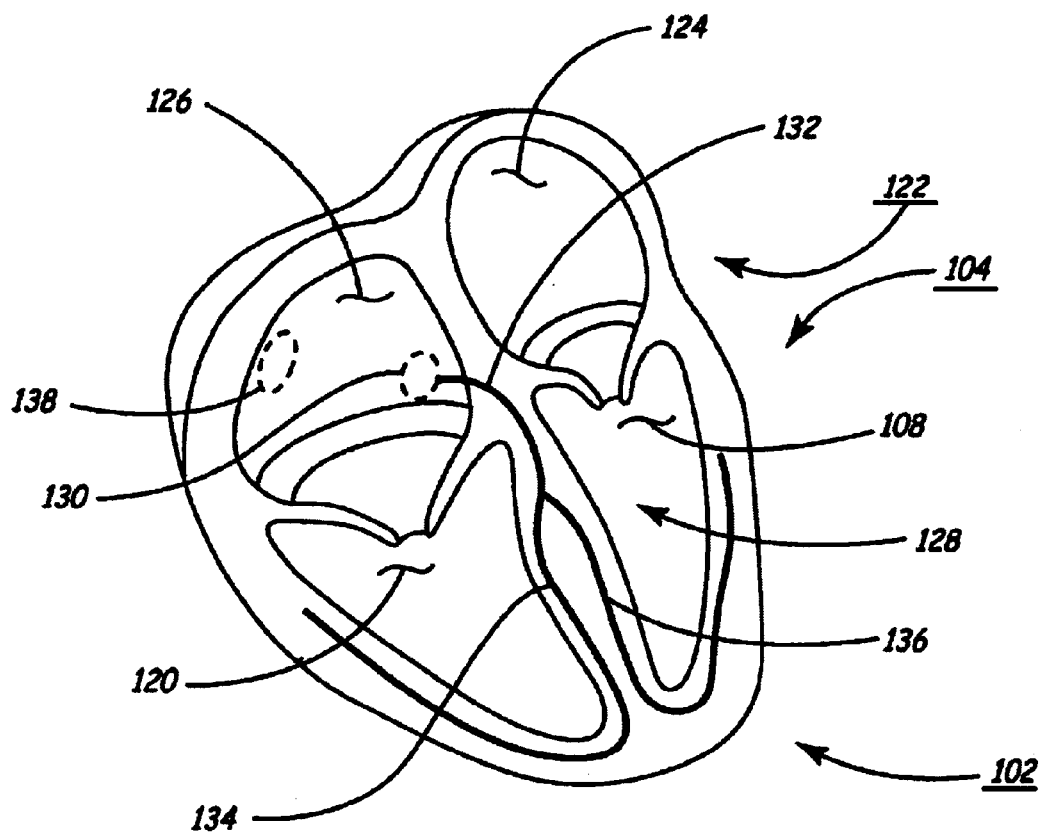
FIG. 1 is a cross-sectional view of a heart having ventricles and atria.

FIG. 1 is a cross-sectional view of a heart 102 having ventricles 108 and 120. In FIG. 1, it may be appreciated that heart 102 includes a conductive path 128 extending between auricle 130 and ventricles 104. In heart 102, conductive path 128 includes an atrioventricular (AV) node 130, a bundle of His 132, a right bundle branch 134, and a left bundle branch 136.

Heart 102 also includes a sinoatrial (SA) node 138. In a healthy heart, the SA node acts as a natural pacemaker controlling the heart rate. At appropriate times, an electrical impulse arising from the SA node is transmitted to the right and left atrial chambers. This impulse causes muscle tissue of the atria to depolarize and contract which results in a P-wave on the electrocardiogram. Impulses propagated from the SA node travel to and through the atrioventricular (AV) node. The impulse from the AV node is transmitted through the bundle of His, the right bundle branch, the left bundle branches, and a plurality of Purkinje fibers that cover most of the endocardial surface of the ventricles. The ventricular muscle tissue depolarizes, then contracts. This forces blood held in the ventricles through the arteries and to various body locations. This action is repeated in a rhythmic cycle in which the atrial and ventricular chambers alternately contract and pump, then relax and fill.

Figure 2:
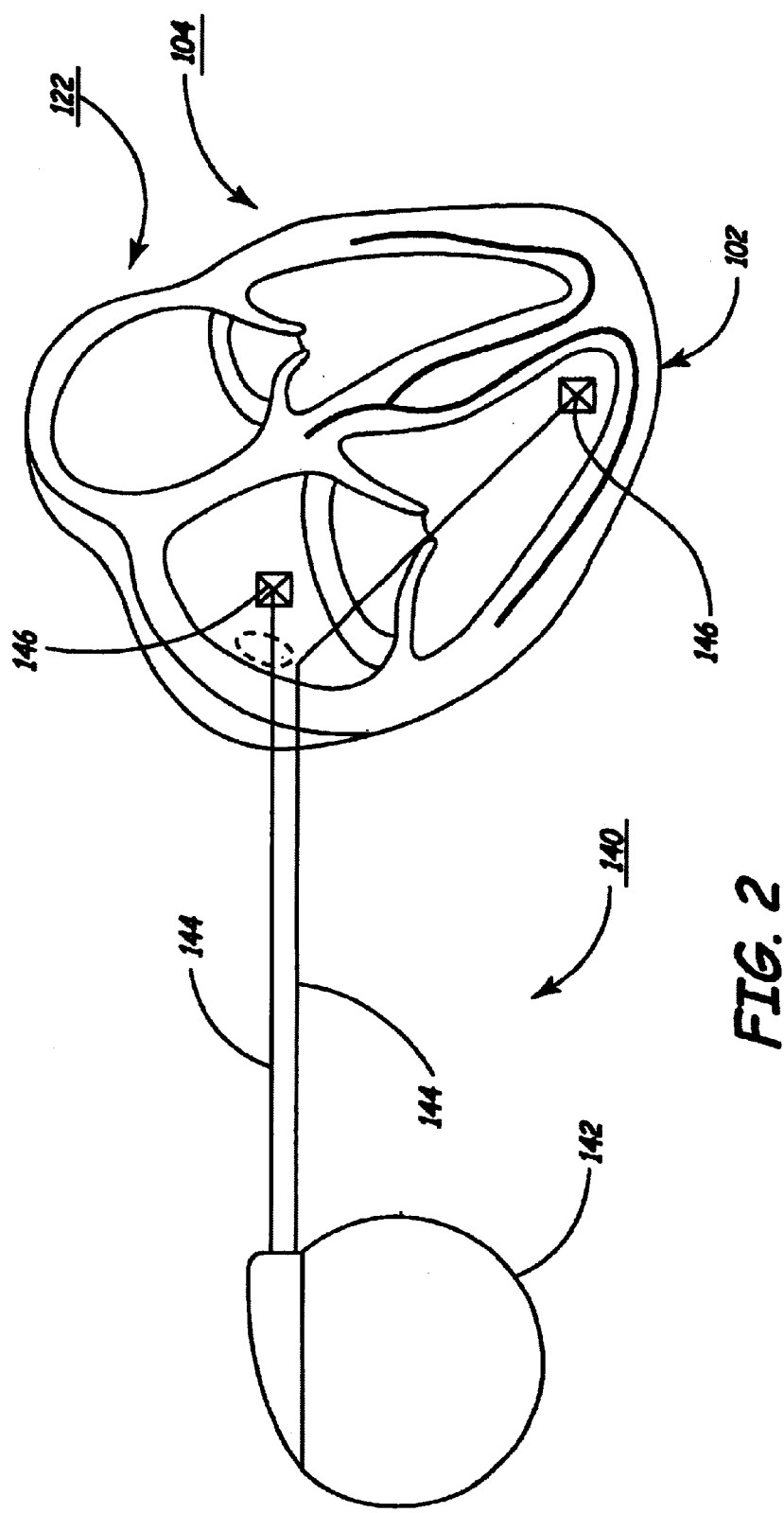
FIG. 2 is a diagrammatic view of a pacing system in accordance with the present invention.

FIG. 2 is a diagrammatic view of a pacing system 140 in accordance with the present invention. Pacing system 140 includes a pacemaker 142 that is coupled to heart 102 of FIG. 1 by a pluarality of leads 144 and electrodes 146. Pacemaker 142 may be used to treat a heart in which the natural pacing system has ceased performing properly. Pacemaker 142 may have a single electrode operation in which pacing current flows between an electrode 146 and a housing of pacemaker 142. Pacemaker 142 may also have a dual electrode operation in which pacing current flows between two or more electrodes.

Some methods in accordance with the present invention may include the step of severing the conductive path between atria 122 and ventricles 104. In some methods, the step of severing the conductive path may include the step of ablating the AV node of a heart. The step of ablating the AV node may be accomplished, for example, using a catheter including an ablation electrode coupled to a source of radio frequency energy. By comparing FIG. 1 and FIG. 2, it may be appreciated that the AV node of heart 102 has been ablated in the embodiment of FIG. 2.

Figure 3:
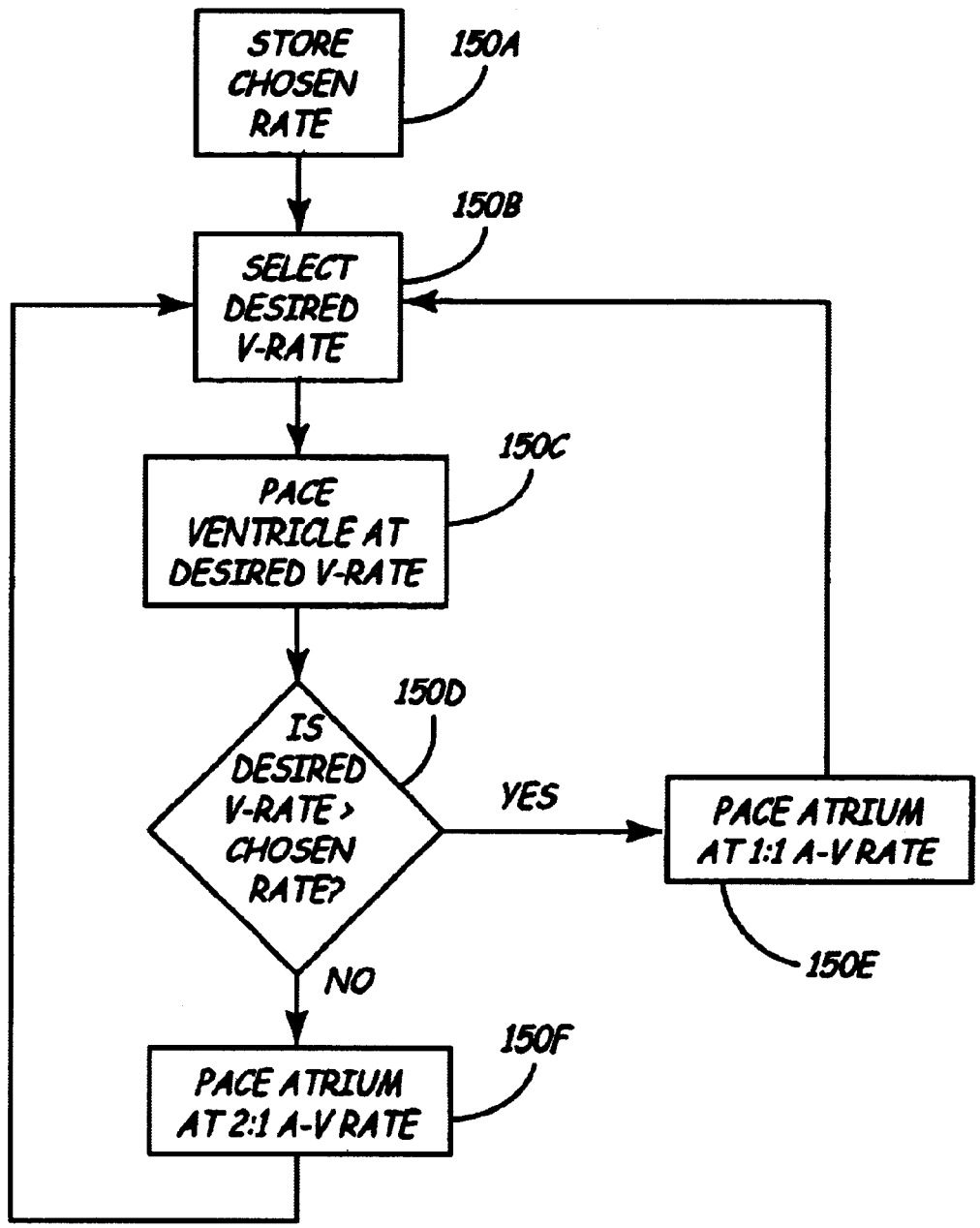
FIG. 3 is a flow diagram illustrating a method of pacing a heart in accordance with the present invention.

FIG. 3 is a flow diagram 148 illustrating a method of pacing a heart in accordance with the present invention. The method of FIG. 3 may be used, for example, in conjunction with pacing system 140 of FIG. 2. At block 150A of flow diagram 148 a preferred rate is selected and stored. In the method of FIG. 3, the preferred rate is used to make decisions relating to the pacing of the heart of a patient. The preferred rate may be selected to match a particular patient, for example, by taking into account physical characteristics of that patient. The preferred rate may be stored, for example, in a memory of pacemaker 142 of pacing system 140 of FIG. 2.

At block 150B of flow diagram 148, a desired ventricular rate is selected. In some methods in accordance with the present invention, the step of selecting the desired ventricular rate may include the steps of sensing spontaneous ventricular signals, and determining a desired ventricular rate in response to the sensed ventricle signals.

At block 150C of flow diagram 148, the ventricle is paced at the desired ventricular rate. Pacing pulses may be delivered to the ventricle, for example, via one or more leads coupled to one or more electrodes. A pulse generator in accordance with the present invention may include one or more capacitors, and a switching circuit capable of charging the capacitor(s) by coupling the capacitor(s) to an energy source and discharging the capacitor(s) through the electrodes.

At block 150D, a determination is made as to whether or not the desired ventricular rate is greater than the preferred rate. In the method of FIG. 3, the atrium will be paced at the desired ventricular rate (block 150E) if the desired ventricular rate is greater than the preferred rate. Also in the method of FIG. 3, the atrium will be paced at twice the desired ventricular rate (block 150F) if the desired ventricular rate is less than the preferred rate.

Figure 4:
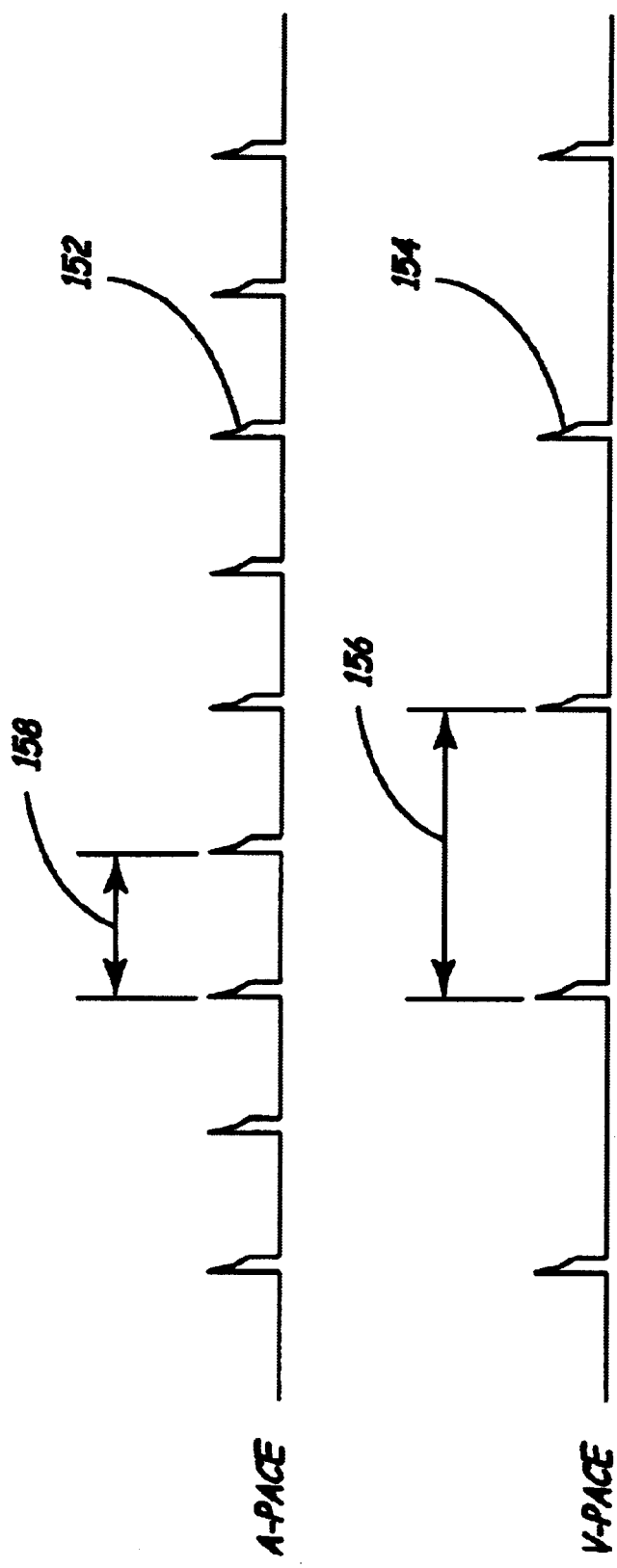
FIG. 4 is a simplified timing diagram illustrating a sequence of atrial pulses and ventricular pulses which may be produced in accordance with an exemplary method of the present invention.

FIG. 4 is a simplified timing diagram illustrating an sequence of atrial pulses 152 and ventricular pulses 154 which may be produced in accordance with an exemplary method of the present invention. In the embodiment of FIG. 4, ventricular pulses 154 are being delivered to at least one ventricle of a heart at a desired ventricular rate. A desired ventricular period 156 associated with the desired ventricular rate is illustrated in FIG. 4.

In the embodiment of FIG. 4, atrial pulses 152 are being delivered to the atria of the heart at a desired atrial rate. A desired atrial period 158 associated with the desired atrial rate is illustrated in FIG. 4. In FIG. 4, atrial period 158 is half the ventricular period 156. Thus, in the embodiment of FIG. 4, the atria are being paced at twice the desired ventricular rate. In FIG. 4 it may be appreciated that the ratio of the atrial rate to the ventricular rate (A-V ratio) may be described as being 2:1.

Figure 5:
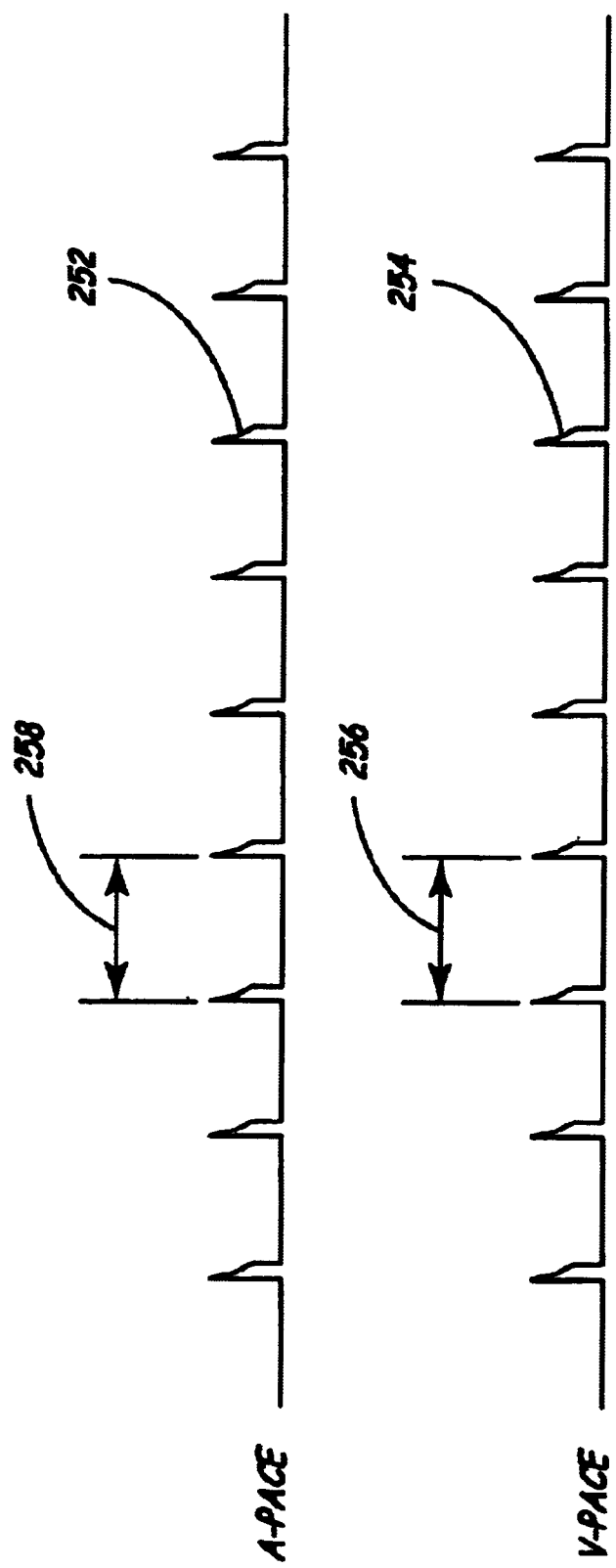
FIG. 5 is a diagrammatic representation of a sequence of atrial pulses and ventricular pulses which may be produced in accordance with an exemplary method of the present invention.

FIG. 5 is a diagrammatic representation of a sequence of atrial pulses 252 and ventricular pulses 254 which may be produced in accordance with an exemplary method of the present invention. In the embodiment of FIG. 5, the atrium and the ventricle are both being paced at a desired ventricular rate. Thus, in FIG. 5, the A-V ratio is 1:1. In the embodiment of FIG. 5, an atrial pulse is delivered approximately substantially synchronous with each ventricle pulse.

Referring again, briefly, to FIG. 4 it may be appreciated that in the method of FIG. 4, a ventricle pulse is delivered synchronously with one out of two atrial pulses. Referring again to FIG. 5, an atrial period 258 and a ventricular period 256 are illustrated in FIG. 5. In FIG. 5 it may be appreciated that atrial period 258 has the same length as ventricular period 256.

In some methods in accordance with the present invention, the atrium is paced at twice the desired ventricular rate (2:1 A-V ratio) while the desired ventricular rate is less than a preferred rate. Also in some methods in accordance with the present invention, the atrium is paced at the desired ventricular rate (1:1 A-V ratio) while the desired ventricular rate is greater than the preferred rate. In some methods, in accordance with the present invention, there is a transition period during which the atrial rate transitions from a 2:1 A-V ratio to a 1:1 A-V ratio. In these methods there may also be a transition period during which the atrial rate transitions from a 1:1 A-V ratio to a 2:1 A-V ratio. During these transition periods, the atrial period may be incrementally changed until the desired A-V ratio is reached.

Figure 6:
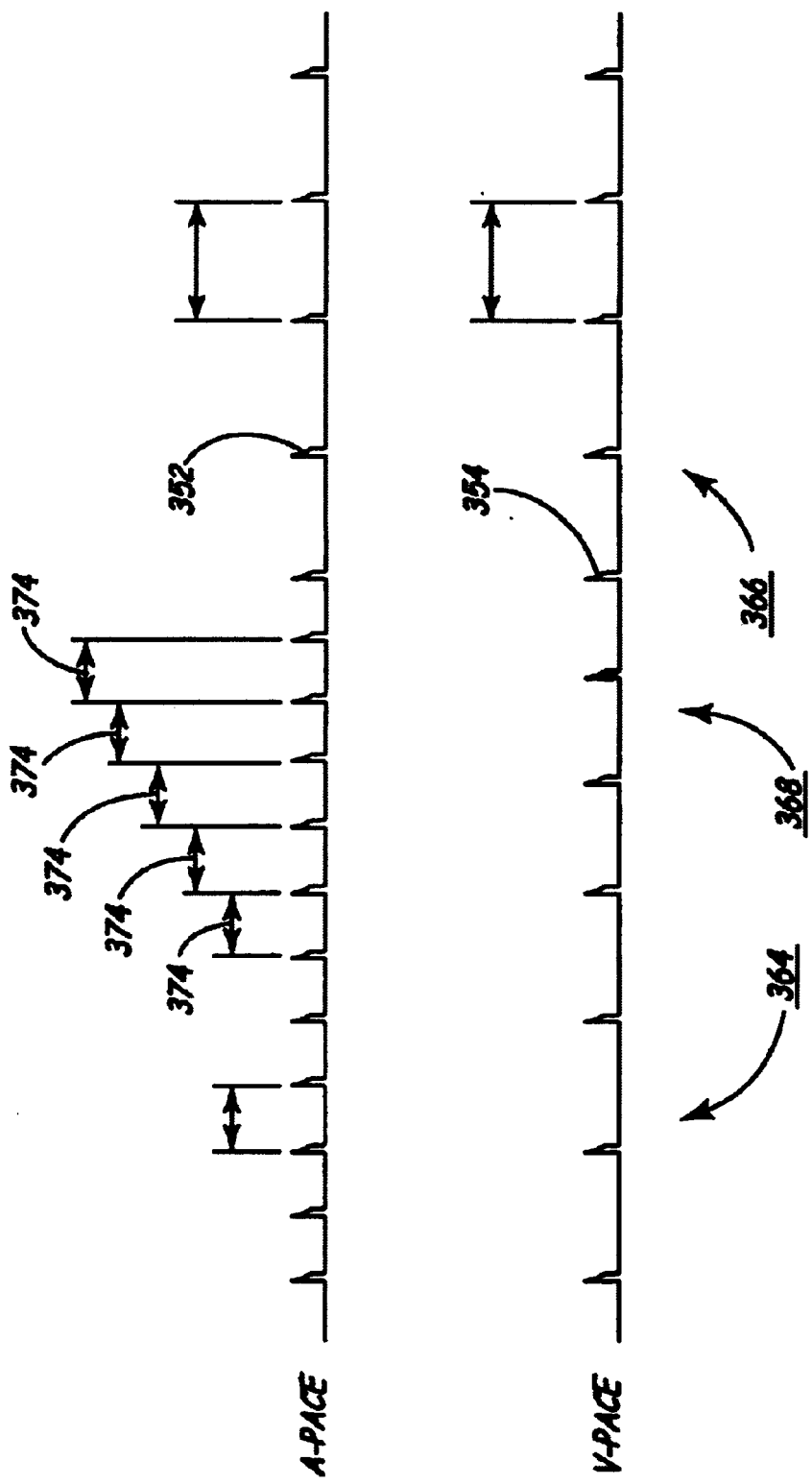
FIG. 6 is a diagrammatic representation of a sequence of atrial pulses and ventricular pulses which may be produced in accordance with an exemplary method of the present invention.

FIG. 6 is a diagrammatic representation of a sequence of atrial pulses 352 and ventricular pulses 354 which may be produced in accordance with an exemplary method of the present invention. FIG. 6 includes a proximal region 364, a distal region 366, and a transition region 368 disposed between proximal region 364 and distal region 366. In the embodiment of FIG. 6, atrial pulses 352 and ventricular pulses 370 of proximal region 364 exhibit an A-V ratio of about 2:1. Also in FIG. 6, atrial pulses 352 and ventricular pulses 354 of distal region 366 exhibit an A-V ratio of 1:1.

In FIG. 6 it may be appreciated that the atrium and the ventricle are being synchronously paced in proximal region 364 and distal region 366. In FIG. 6 it may also be appreciated that the atrium and the ventricle are being asynchronously paced in transition region 368. In the embodiment of FIG. 6, the atrial pulses 352 disposed in transitional region 368 are separated by transitional pacing periods 374. Methods in accordance with the present invention are possible in which these transitional pacing periods 374 are incrementally changed until a desired A-V ratio is obtained. Methods in accordance with the present invention are possible in which the atrial rate is slowly incremented until A-V synchrony is reached.

Figure 7:
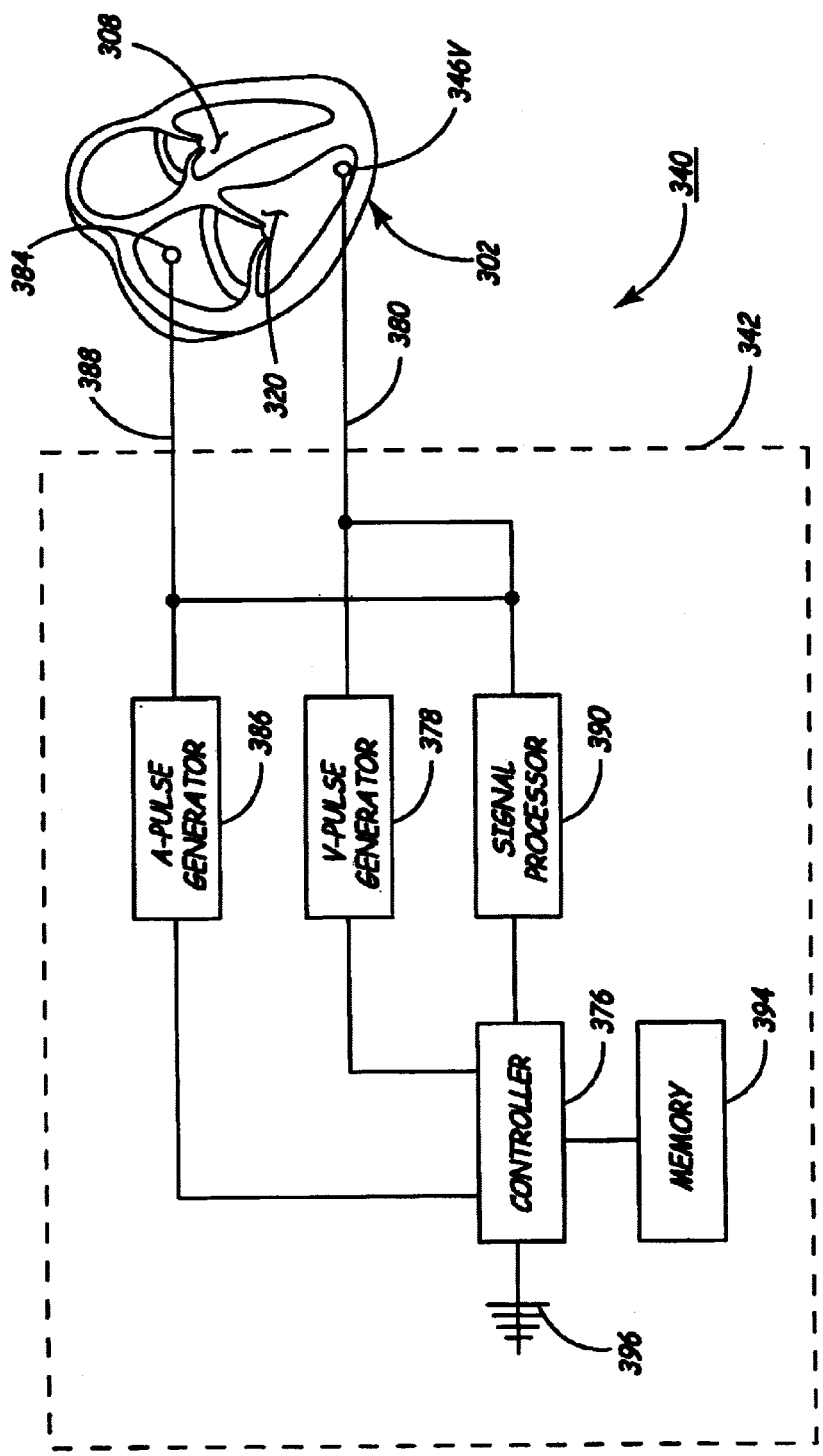
FIG. 7 is a block diagram of a pacing system in accordance with an exemplary embodiment of the present invention.

FIG. 7 is a block diagram of a pacing system 340 in accordance with an exemplary embodiment of the present invention. As shown in FIG. 7, pacing system 340 comprises a pacemaker 342 including a controller 376. Controller 376 may comprise, for example, a microprocessor.

A ventricular pulse (VP) generator 378 of pacemaker 342 provides pacing pulses, generated under the control of controller 376, for delivery through a ventricle pulse VP-lead 380 to one or more ventricular electrodes 346. In the embodiment of FIG. 7, a ventricular electrode 346 is shown disposed in a right ventricle 320 of a heart 302. It is to be appreciated that methods and apparatus in accordance with the present invention may be used with multiple chamber pacing. Thus, in some applications, one or more ventricular electrodes may also be located in or near a left ventricle 308 of heart 302. An atrial pulse generator 386 of pacemaker 342 provides atrial pulses, also generated under the control of controller 376, for delivery through an atrial pulse AP-lead 388 to one or more atrial electrodes 384. Atrial pulse generator 386 and ventricular pulse generator 378 may each include one or more capacitors, and a switching circuit capable of charging the capacitor(s) by coupling the capacitor(s) to an energy source and discharging the capacitor(s) through the electrodes.

Pacemaker 342 also includes a signal processor 390 which may be used to sense and process spontaneous signals from heart 302. For example, signals may be sensed from right atrium 326 via atrial electrode 384. By way of a second example, signals from right ventricle 320 may be sensed via ventricular electrode 346. A method in accordance with the present invention may include the steps of sensing spontaneous signals from heart 302 and determining a desired ventricular rate in response to the sensed ventricle signals. Signal processor 390 may comprise, for example, one or more amplifiers, and one or more filters.

Pacemaker 342 also includes a memory 394. Memory 394 may be used to store operating instructions for controller 376. Memory 394 may also be used to store values in accordance with the present invention. Examples of values which may be stored include a preferred rate and a desired ventricular rate. Pacemaker 342 also includes a telemetry antenna 396. Telemetry antenna may be used, for example, to load instructions and values into memory 394 via controller 376.

Figure 8:
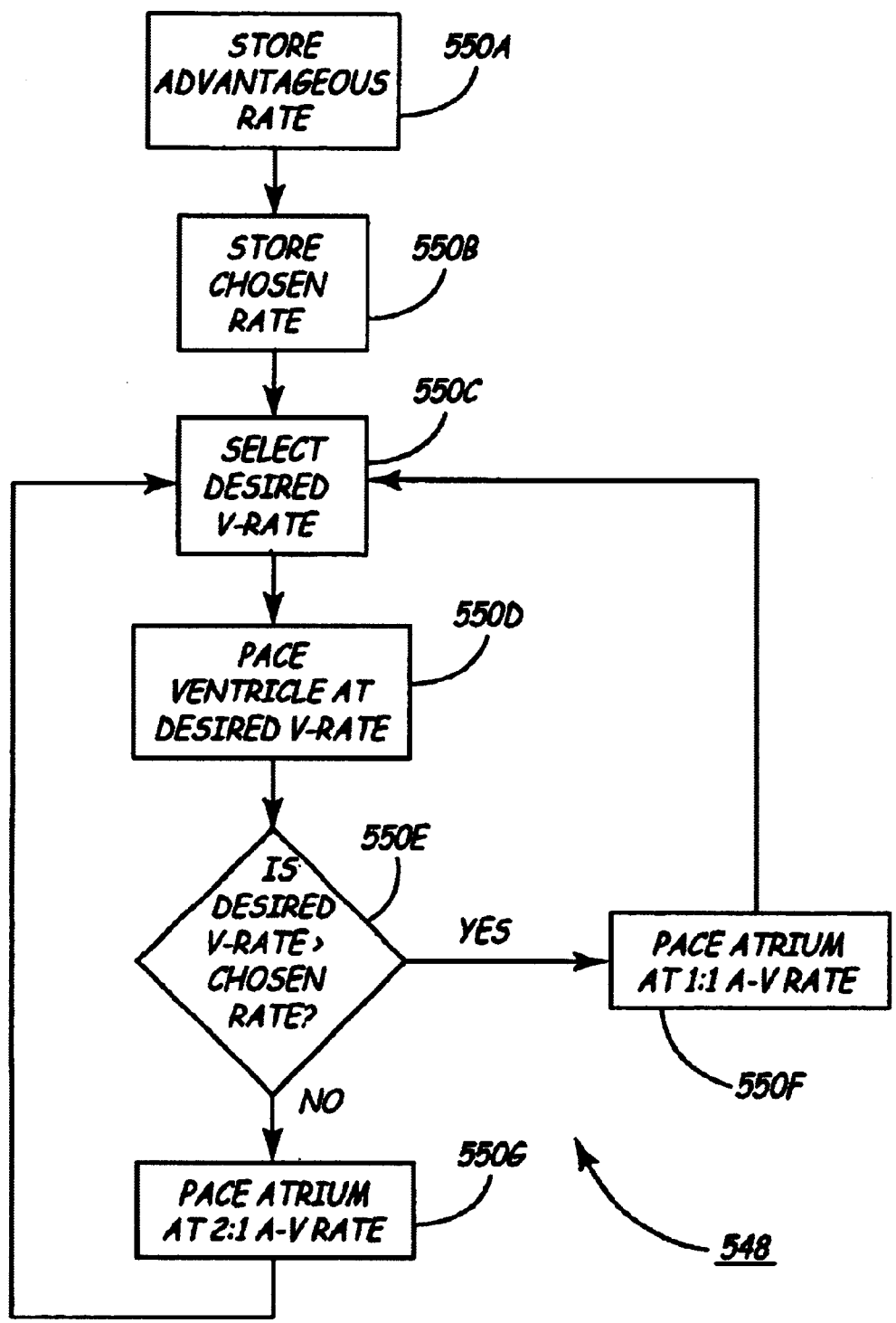
FIG. 8 is a flow diagram illustrating a method of pacing a heart in accordance with the present invention.

FIG. 8 is a flow diagram 548 illustrating a method of pacing a heart in accordance with the present invention. The method of FIG. 8 may be used, for example, in conjunction with pacing system 540 of FIG. 7. At block 550A of flow diagram 548 an advantageous rate is selected and stored. The advantageous rate may be stored, for example, in memory 594 of pacemaker 542 of pacing system 540 of FIG. 7.

At block 550B of flow diagram 548 a preferred rate is selected and stored. In a useful embodiment of the present method, the preferred rate may be chosen from a range of between about 60 beats per minute and about 100 beats per minute. The preferred rate may be selected to match a particular patient, for example, by taking into account physical characteristics of that patient. In some embodiments, the preferred rate may be, for example, about 80 beats per minute. In the method of FIG. 8, the preferred rate is used to make decisions relating to the pacing of the heart of a patient.

At block 550C of flow diagram 548, a desired ventricular rate is selected. In some methods in accordance with the present invention, the step of selecting the desired ventricular rate may include the steps of sensing spontaneous ventricular signals, and determining a desired ventricular rate in response to the sensed ventricle signals.

At block 550D of flow diagram 548, the ventricle is paced at the desired ventricular rate. Pacing pulses may be delivered to the ventricle, for example, via one or more leads coupled to one or more electrodes. The method of FIG. 8 also includes the step of pacing the atrium, however, the atrial rate is selected based upon a determination made at block 550E.

At block 550E, a determination is made as to whether or not the desired ventricular rate is greater than the preferred rate. In the method of FIG. 8, the atrium will be paced at the advantageous pacing rate (block 550F) if the desired ventricular rate is greater than the preferred rate. Also in the method of FIG. 8, the atrium will be paced at twice the desired ventricular rate (block 550G) if the desired ventricular rate is less than the preferred rate.

In a preferred embodiment, the advantageous rate is selected to be fast enough to reduce the likelihood that atrial fibrillation will occur. The advantageous rate may be selected to match a particular patient, for example, by taking into account physical characteristics of that patient. In a useful embodiment of the present method, the advantageous rate may be chosen from a range of between about 120 beats per minute and about 180 beats per minute. In some embodiments, the preferred rate may be, for example, about 160 beats per minute.

Several forms of invention have been shown and described, and other forms will now be apparent to those skilled in art. It will be understood that embodiments shown in drawings and described above are merely for illustrative purposes, and are not intended to limit the scope of invention defined claims which follow.

What is claimed is:

1. A method for reducing the likelihood of atrial fibrillation in a heart, the method comprising the steps of:

selecting a desired ventricular rate;

pacing a ventricle of the heart at the desired ventricular rate;

pacing an atrium of the heart at twice the desired ventricular rate while the desired ventricular rate is less than a preferred rate; and pacing the atrium of the heart at the desired ventricular rate while the desired ventricular rate is greater than the preferred rate.

2. The method of claim 1, wherein the preferred rate is between about 60 beats per minute and about 100 beats per minute.

3. The method of claim 2, wherein the preferred rate is about 80 beats per minute.

4. The method of claim 1, wherein the step of selecting the desired ventricular rate includes the steps of sensing spontaneous ventricular signals, and determining a desired ventricular rate in response to the sensed ventricle signals.

5. The method of claim 1, wherein an atrial pulse is delivered synchronously with each ventricle pulse.

6. The method of claim 1, wherein a ventricular pulse is delivered synchronously with each atrial pulse while the desired ventricular rate is greater than the preferred rate.

7. The method of claim 1, wherein a ventricle pulse is delivered synchronously with one out of two atrial pulses while the desired ventricular rate is less than the preferred rate.

8. A pacing system for reducing incidence of atrial fibrillation in a heart, the pacing system comprising:

means for selecting a desired ventricular rate;

means for pacing a ventricle of the heart at the desired ventricular rate; and means for pacing an atrium of the heart at twice the desired ventricular rate while the desired ventricular rate is less than a preferred rate and pacing the atrium of the heart at the desired ventricular rate while the desired ventricular rate is greater than the preferred rate.

9. A method for reducing the likelihood of atrial fibrillation in a heart, the method comprising the steps of:

selecting an advantageous atrial rate;

selecting a desired ventricular rate;

pacing the ventricle of the heart at the desired ventricular rate;

pacing the atrium of the heart at twice the desired ventricular rate while the desired ventricular rate is less than a preferred rate; and pacing the atrium of the heart at an advantageous atrial rate while the desired ventricular rate is greater than the preferred rate.

10. The method of claim 9, wherein the advantageous atrial rate is between about 120 beats per minute and about 180 beats per minute.

11. The method of claim 10, wherein the advantageous atrial rate is about 160 beats per minute.

12. The method of claim 9, wherein the preferred rate is between about 60 beats per minute and about 100 beats per minute.

13. The method of claim 12, wherein the preferred rate is about 80 beats per minute.

14. The method of claim 9, wherein the step of selecting the desired ventricular rate includes the steps of sensing spontaneous ventricular signals, and determining a desired ventricular rate in response to the sensed ventricle signals.

15. The method of claim 9, wherein an atrial pulse is delivered synchronously with each ventricle pulse.

16. The method of claim 9, wherein a ventricular pulse is delivered synchronously with each atrial pulse while the desired ventricular rate is greater than the preferred rate.

17. The method of claim 9, wherein a ventricle pulse is delivered synchronously with one out of two atrial pulses while the desired ventricular rate is less than the preferred rate.

18. A pacing system for reducing atrial fibrillation in a heart, the pacing system comprising:

means for selecting a desired ventricular rate;

means for pacing a ventricle of the heart at the desired ventricular rate; and means for pacing an atrium of the heart at twice the desired ventricular rate while the desired ventricular rate is less than a preferred rate, and pacing the atrium of the heart at an advantageous rate while the desired ventricular rate is greater than the preferred rate.

* * * * *